| (12) | United States Patent | (10) Patent No.: | US 10,357,240 B1 |
|---|---|---|---|
| | Tomas | (45) Date of Patent: | Jul. 23, 2019 |

(54) HERNIA SURGERY METHOD AND SYSTEM

(71) Applicant: Robert M. Tomas, Fort Myers, FL (US)

(72) Inventor: Robert M. Tomas, Fort Myers, FL (US)

( * ) Notice: Subject to any disclaimer, the term of this patent is extended or adjusted under 35 U.S.C. 154(b) by 504 days.

(21) Appl. No.: 14/968,879

(22) Filed: Dec. 14, 2015

Related U.S. Application Data

(60) Provisional application No. 62/091,529, filed on Dec. 13, 2014.

(51) Int. Cl.
*A61B 17/04* (2006.01)
*A61B 17/00* (2006.01)

(52) U.S. Cl.
CPC .... *A61B 17/04* (2013.01); *A61B 2017/00743* (2013.01)

(58) Field of Classification Search
CPC .......... A61B 17/04; A61B 2017/00743; A61B 17/0401; A61B 2017/0403–0464; A61F 2/0063; A61F 2002/0068; A61F 2002/0072
USPC ........................................................ 606/151
See application file for complete search history.

(56) References Cited

U.S. PATENT DOCUMENTS

| 3,633,582 | A | * | 1/1972 | Steinman | ............... | A61B 17/02 |
| | | | | | | 606/148 |
| 4,452,245 | A | * | 6/1984 | Usher | .................... | A61B 17/04 |
| | | | | | | 606/151 |
| 5,730,994 | A | * | 3/1998 | Askill | ..................... | A61L 15/24 |
| | | | | | | 424/402 |
| 2010/0217316 | A1 | * | 8/2010 | Fedinec | ........... | A61B 17/06166 |
| | | | | | | 606/228 |

FOREIGN PATENT DOCUMENTS

| RU | 2426501 C1 | 8/2011 |
| RU | 2498782 C1 * | 11/2013 |

OTHER PUBLICATIONS

"The Technique of the Closure of Laparotomy Incisions". Journal of Obstetrics and Gynecology; Jun. 1926, pp. 300-312.*
"Modified Technique for Mayo's Repair of Umbilical and Paraumbilical Hernia". Medical Journal of Babylon; 2006, vol. 3, No. 3-4.*
Machine Translation of RU 2498782 C1.*
Kudur MH, PAi SB, Sripathi H, Prabhu S. Sutures and suturing techniques in skin closure. Indian J Dermatol Venereol Leprol 2009; 75:425-34. (Year: 2009).*
Wulf. H. Utian, M.B., B.CH., Umbilical Hernia Containing a Pregnant Uterus at Term, S.A. Tydskrif Vir Obstetrie En Ginekologie, Jun. 1, 1968, pp. 18-20.
Karim Al-Araji, Modified Technique for Mayo's Repair of Umbilical and Paraumbilical Hernia, Medical Journal of Babylon—2006 vol. 3 No. 3-4, pp. 255-259.
Melissa Brown, Code Fat Albert's Hernia Repair in 5 Easy Steps, https://www.aapc.com/blog/23519-code-fat-alberts-hernia-repair-in-5-easy-steps/.

* cited by examiner

*Primary Examiner* — Kathleen S Holwerda
(74) *Attorney, Agent, or Firm* — Avery, Whigham & Winesett, P.A.; Nathan Stamey Winesett

(57) ABSTRACT

The present invention discloses a suturing method and system 10 for repairing hernia. The method comprises applying multiple layers of sutures for closing a primary defect 101. The invention comprises a suturing means for strengthening the repair by securing the primary defect to non-damaged tissue 120 The method of the present invention can decrease the chances of recurring hernia.

14 Claims, 2 Drawing Sheets

HERNIA SURGERY METHOD AND SYSTEM

CLAIM OF PRIORITY

This application is based on and claims the benefit of priority from U.S. provisional application No. 62/091,529 filed Dec. 13, 2014.

STATEMENT REGARDING FEDERALLY SPONSORED RESEARCH/DEVELOPMENT

Not Applicable.

BACKGROUND OF THE INVENTION

Field of the Invention

The present invention relates to a method for repairing hernia.

Related Art

A hernia is an anatomical defect. Hernias can occur when an organ protrudes through the wall of its containing cavity. Hernias can be caused due to the weakening of the localized musculature (fascia) and exertion of pressure on the internal organs. There are several types of hernias depending upon the location and the tissue involved e.g. inguinal, femoral, diaphragmatic, umbilical, ventral, incisional, etc.

Umbilical hernias occur in the navel (umbilicus) region. During fetal development, nutrients are delivered through the umbilical cord, which enters through the umbilicus region. After birth, the umbilical cord can be cut from the navel. Umbilical hernias can occur in children and usually regress by the age of 4-5 years. If the umbilical hernia does not regress or is painful or grows in size, it can be surgically repaired. In adults, hernias can be caused due to heavy lifting or due to obesity where the core can push out. Ventral hernias are a type of abdominal hernia. They may occur due to a congenital defect or develop as a result of trauma to the abdominal region. Incisional hernias can be caused when a surgical incision doesn't heal properly. The size of a hernia can range from a marble-size to the size of a golf ball. Hernias can be repaired when they become painful or increase in size.

Several methods exist to repair hernias. Repairs can be carried out by surgically accessing the hernia sac, pushing or excising the hernia sac, and suturing the defect. Mesh may be employed to strengthen the defective tissue to prevent recurrence of the hernia. However, using a mesh, which is a foreign object, may result in undesired complications, such as chronic pain, infections, rejection of the mesh by the body, nerve and blood vessel injuries, or injury to nearby organs.

Umbilical or ventral hernia repairs using mesh techniques can have a recurrence rate of 4-10%. Recurrence rates using conventional no mesh techniques can be 15-40%.

SUMMARY OF THE INVENTION

It has been recognized that it would be advantageous to develop a new method for repairing hernias to provide additional strength to the repair without the use of mesh and to lessen recurrence rates and reduce complications from repairs.

The present invention provides for a method for repairing anatomical defects such as hernias using multi-layered sutures without the use of a mesh.

The present invention further provides for a method for repairing hernias that employs multi-layered suturing. The suturing method can comprise applying a first layer of running continuous sutures to close a primary defect; applying a second layer of vertical mattress sutures along the primary defect; and applying a third layer of running continuous sutures. The second layer of vertical mattress sutures can be applied perpendicularly along an axis formed by the primary defect. The second layer can include vertical mattress sutures applied to non-damaged tissue superior to and inferior to the primary defect along the axis of the primary defect. This second layer can extend at least two inches superiorly and inferiorly beyond the primary defect into the non-damaged tissue. The third layer of running continuous sutures can be a first running continuous suture running from non-damaged tissue superior to the primary defect that meets and is tied to a second running continuous suture running from non-damaged tissue inferior to the primary defect. This third layer can extend at least two inches beyond the primary defect superiorly and inferiorly into the non-damaged tissue. This third layer can be stitched in between the vertical mattress sutures of the second layer.

The invention can provide for a suturing method used for repairing hernias such as inguinal, femoral, diaphragmatic, umbilical, ventral, incisional hernia.

The invention can provide for a multi-layered suturing method that can comprise applying a first layer of running continuous sutures to close a primary defect that has a superior end and an inferior end and an axis formed thereby. The axis can have a superior pole region and an inferior pole region that is located in non-damaged tissue beyond the superior and inferior ends of the primary defect, respectfully. The axis can have a mid-pole region between the superior and inferior ends. Then a second layer of vertical mattress sutures can be applied along and across the axis of the primary defect and extend from the superior pole region to the inferior pole region. Then a third layer of sutures can be applied along the axis of the primary defect by suturing a first suture from the superior pole region to the mid-pole region and suturing a second suture from the inferior pole region to the mid-pole region and tying them together at the mid-pole region.

The superior pole region can extend up to three inches beyond the superior end of the primary defect and the inferior pole regions can extend up to three inches beyond the inferior end of the primary defect. The superior and inferior pole regions can extend approximately two to three inches beyond the superior and inferior ends of the primary defect, respectfully. The superior and inferior pole regions can extend at least two inches beyond the superior and inferior ends of the primary defect.

The third layer of sutures can be stitched in between the vertical mattress sutures of the second layer. The third layer can be two running continuous sutures that converge and are tied at the mid-pole of the primary defect.

The invention can provide for a suturing method wherein the first layer is composed of a first non-absorbable suture material, the second layer is composed of a second non-absorbable material and the third layer is composed of a third non-absorbable material.

The invention can provide for a suturing method wherein the first, second and third non-absorbable materials can be independently selected from the group comprising polypropylene, polyester, nylon, polyvinylidene fluoride (PVDF), polyethylene, blends of polyvinylidene fluoride and polyvinylidene fluoride-co-hexafluoropolypropylene, Dacron or the like.

The invention can provide for a system for hernia repair having a running continuous suture for closing a primary defect of a hernia, a plurality of vertical mattress sutures along the primary defect, and a suturing means for strengthening the repair. The suturing means can secure the primary defect to non-damaged tissue at least two inches superior to the primary defect and at least two inches inferior to the primary defect.

The invention can provide for a multi-layered suturing method for high pressure areas that reduces the recurrence rate of the hernia. The invention can provide a three-layered suture technique that can disperse the core pressure along a longer axis of tension, which can lower the recurrence rate for hernias.

The method of the present invention can address the need for a suturing technique for hernia repairs to overcome complications of conventional surgical hernia repair techniques. The present invention can provide for a suturing method for hernia repair. The method of the present invention can make use of multi-layered suturing technique for repairing the hernia.

The multi-layered suturing technique can provide increased strength of the hernia repair and thus a reduced recurrence rate.

The invention can also provide for a no mesh hernia repair having a recurrence rate of not more than 4%. The invention can provide a recurrence rate for repairing umbilical, ventral, and incisional hernias without mesh can be not more than 4%.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

Embodiments of the present invention hereinafter described in conjunction with the appended drawings are provided to illustrate and not to limit the present invention, wherein like designations denote like elements, and in which.

DETAILED DESCRIPTION

Figure 1:
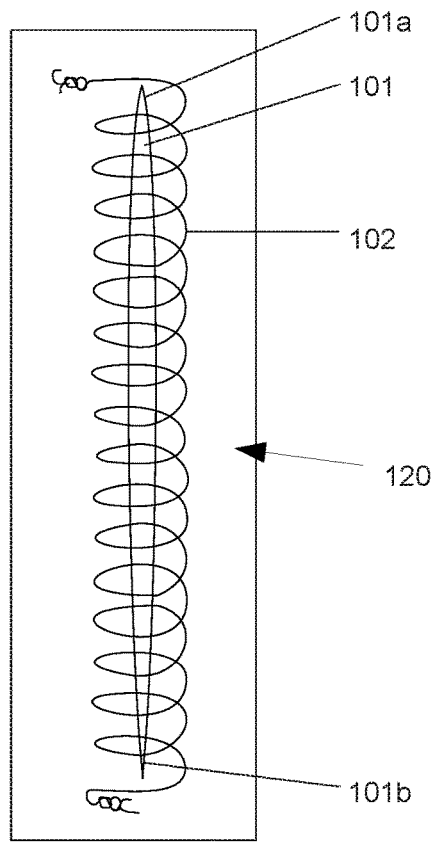
FIG. 1 shows a front view of a hernia repair 10 in accordance with an embodiment of the present invention showing a first layer of running continuous sutures 102 to close a primary defect 101, with the tissue 120 made transparent for viewing the repair and the sutures shown in expanded, non-tightened form for clarity.

From the foregoing detailed description of certain embodiments, it will be apparent that various modifications, additions and other alternative embodiments are possible without departing from the true scope and spirit of the invention. The embodiments discussed were chosen and described to provide the best illustration of the principles of the invention and its practical application to thereby enable one of ordinary skill in the art to use the invention in various embodiments and with various modifications as are suited to the particular use contemplated. All such modifications and variations are within the scope of the invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The term "primary defect" implies a hernia or an incision placed in fascia or body tissue for accessing the hernia.

As illustrated in the Figures, a method for repairing hernias is shown. FIG. 1 shows a primary defect 101 in the abdominal region. This primary defect can have a superior end 101a and an inferior end 101b. This primary defect can be an umbilical, ventral, or incisional hernia, or an incision for treating such hernias. In other embodiments, the primary defect can also be an inguinal, femoral, or diaphragmatic hernia. The primary defect 101 can be closed by applying a first layer of sutures 102 as shown in the FIG. 1. According to an embodiment of the present invention, the first layer of sutures 102 is a running continuous type of suture which can close the primary defect 101 of the hernia or incision made on the fascia for accessing the hernia.

Figure 2:
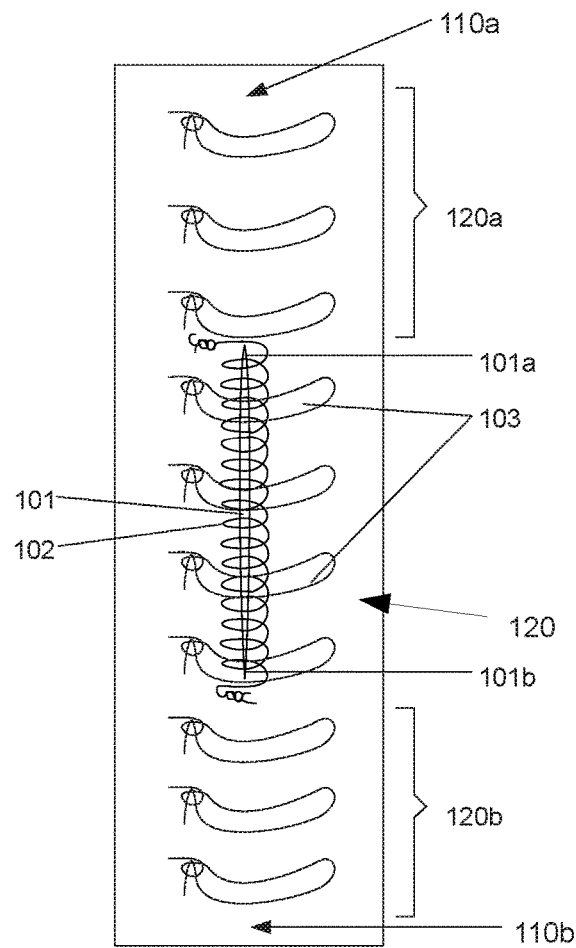
FIG. 2 shows a front view of a hernia repair 10 in accordance with an embodiment of the present invention with a first layer 102 and second layer of vertical mattress type sutures 103, with the tissue 120 made transparent for viewing the repair and the sutures shown in expanded, non-tightened form for clarity.

FIG. 2 depicts the repair of FIG. 1 with the application of a second layer of sutures 103. The second layer of sutures can be a plurality of vertical mattress type sutures 103 applied along the primary defect 101. The use of vertical mattress sutures can provide closure of the deeper layers of the primary defect and can provide additional strength to the repair around the axis 200 of the primary defect. As shown, each vertical mattress suture 103 can be applied perpendicularly to the axis 200 of the primary defect 101 and the first layer of sutures 102. As shown in FIG. 2, the second layer of sutures 103 can be applied under the primary defect 101 and the first layer of sutures 102 along the axis 200 of the primary defect. The second layer of sutures 103 can extend up to non-damaged tissue 120a above the superior end 101a and in non-damaged tissue 120b below the inferior end 101b of the primary defect 101. The extended layer of vertical mattress sutures 103 in the non-damaged tissues 120a and 120b can provide increased strength to the hernia repair by dispersing the core pressure along a longer axis of tension. This can strengthen the repair and lower the recurrence rate of hernia.

Figure 3:
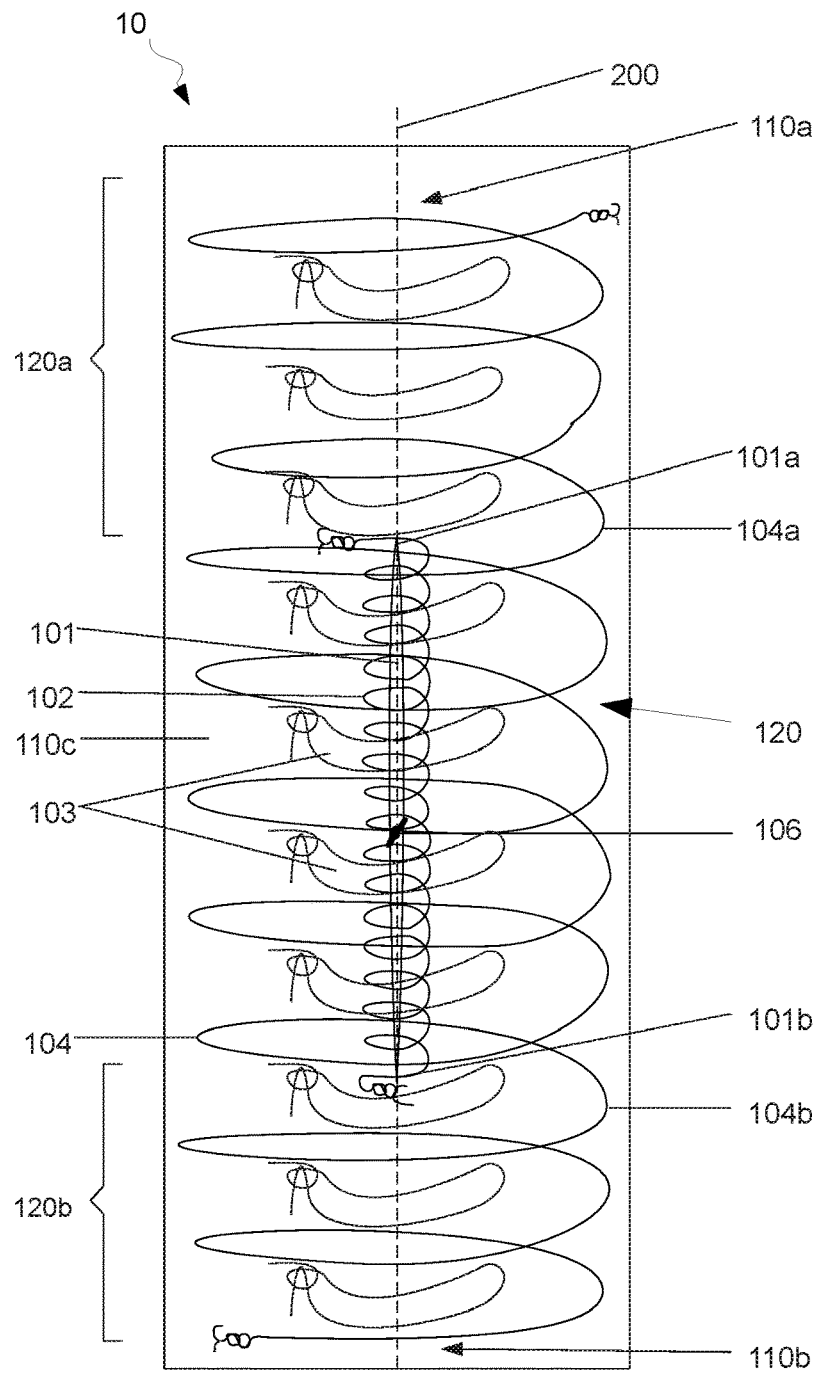
FIG. 3 shows a front view of a hernia repair 10 in accordance with an embodiment of the present invention with the first layer 102, the second layer 103, and a third layer of running continuous sutures 104, showing a first running continuous suture 104a running from non-damaged tissue superior 120a to the primary defect 101 and a second running continuous suture 104b running from non-damaged tissue inferior 120b to the primary defect that meet and are tied together at a mid-pole region 106, with the tissue 120 made transparent for viewing the repair and the sutures shown in expanded, non-tightened form for clarity.

FIG. 3 depicts the repair of FIGS. 1 and 2 with the application of a third layer of sutures 104. FIG. 3 shows the primary defect 101, the superior end 101a of the primary defect, and the inferior end 101b of the primary defect. The figure also illustrates different pole regions of the repair associated with an axis 200 of the primary defect 101. A superior pole region 110a is shown in the non-damaged tissue 120a beyond the superior end 101a of the primary defect 101. An inferior pole region 110b is shown in the non-damaged tissue 120b beyond the inferior end 101b of the primary defect 101. A mid-pole region 110c is also shown over the primary defect between the superior and inferior pole regions.

The third layer of sutures 104 can extend up to non-damaged tissue 120a above the superior end 101a and in non-damaged tissue 120b below the inferior end 101b of the primary defect 101. The extension of the third layer into the non-damaged tissues 120a and 120b can provide increased strength to the hernia repair by dispersing the core pressure along a longer axis of tension. This can strengthen the repair and lower the recurrence rate of hernia.

According to an embodiment of the present invention, the second layer and/or the third layer of sutures 103 can extend into the non-damaged tissue 120a of the superior pole region 110a and the non-damaged tissue 120b of the inferior pole region 110b. This can help secure the repair with non-damaged tissue. In one embodiment, the second and third layers can extend approximately three inches above and approximately three inches below the primary defect 101 securing the repair into the non-damaged tissue of the superior and inferior pole regions. In another embodiment, the second and third layers can extend at least two inches beyond the superior end of the primary defect and at least two inches beyond the inferior end of the primary defect into the non-damaged tissue of the superior and inferior pole regions. According to another embodiment, the second and third layers can extend approximately two to three inches beyond the superior and inferior ends of the primary defect into the non-damaged tissue of the superior and inferior pole regions, respectfully.

FIG. 3 further depicts the application of a third layer of sutures 104 to the primary defect 101, the first layer of sutures 102 and the second layer of sutures 103. In the embodiment shown, a first layer of running continuous sutures 102 closes the primary defect 101. A second layer of a plurality of vertical mattress sutures is applied along and across the axis of the primary defect extending from the superior pole region 110a to the inferior pole region 110b. A third layer of sutures 104 is applied along the axis 200 of the primary defect 101. As shown, the third layer can be applied by suturing a first suture 104a from the superior pole region 110a to the mid-pole region 110c and by suturing a second suture 104b from the inferior pole region 110b to the mid-pole region, and tying the first suture 104a and the second suture 104b together at the mid-pole region 110c as shown by a knot 106. As also shown, the third layer of sutures 104 can be running continuous type sutures stitched in between the vertical mattress sutures 103 of the second layer.

According to another embodiment of the present invention, a system 10 for hernia repair is disclosed as shown in FIG. 3. The system comprises a running continuous suture 102. The running continuous suture can close the primary defect 101. The system further comprises a plurality of vertical mattress sutures 103 along the primary defect. The system further comprises a suturing means 102 and/or 103 for strengthening the repair. The suturing means can secure the primary defect to non-damaged tissue 120. According to one embodiment of the present invention, the suturing means secures the primary defect 101 to non-damaged tissue 120a and 120b at least two inches superior to the primary defect and at least two inches inferior to the primary defect.

The suturing means can include the extension of the second layer into the non-damaged tissue of the superior 110a and inferior pole regions 110b. The suturing means can also include the extension of the third layer into the non-damaged tissue of the superior 110a and inferior pole regions 110b.

According to an embodiment of the present invention, the first layer of suture 102 is composed of a first non-absorbable material, the second layer is composed of a second non-absorbable material, and the third layer is composed of a third non-absorbable material. The first, second and third non-absorbable materials can be non-absorbable sutures. The first, second and third non-adsorbable materials can be independently selected from the group comprising polypropylene, polyester, nylon, polyvinylidene fluoride (PVDF), polyethylene, blends of polyvinylidene fluoride and polyvinylidene fluoride-co-hexafluoropolypropylene, Dacron or the like. However, the suture materials are used herein just for exemplary purposes and not to limit the scope of the invention and any other non-absorbable suture material known to a person of ordinary skill in the art can be used without departing from the scope of the present invention.

According to another exemplary embodiment of the invention, same non-absorbable material can be used for first layer of sutures 102 and the third layer of sutures 104 and is different from the second non-absorbable material used for the second layer of vertical mattress sutures.

The different non-absorbable materials used can be of varied thickness depending upon the type of primary defect and strength required for the hernia repairs.

The multi-layered suturing method of the present invention can be particularly useful for high pressure areas and reduces the recurrence rate of the hernia. The three layered suture technique can disperse the core pressure along a longer axis of tension, therefore lowering the recurrence rate for hernias. The recurrence rate for hernia repairs without mesh can be not more than 4%. The recurrence rate for umbilical, ventral, and incisional hernia repairs can be 4% or less.

Thus, the method of the present invention can be beneficial to reduce the recurrence of the hernia. Further, the method of the present invention can provide extra strength to the high tension areas. Also, there can be lesser probability of post surgery complications using this method that requires no mesh.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

What is claimed is:

1. A suturing method for repairing hernia without surgical mesh comprising:
   a) applying a first layer of running continuous sutures to close a primary defect in a fascia of the hernia, wherein the primary defect has a superior end and an inferior end and an axis formed thereby;
   b) applying a second layer comprising a plurality of vertical mattress sutures in the fascia along the primary defect, wherein the second layer extends superiorly and inferiorly to non-damaged tissue at least two inches beyond the superior end and the inferior end, respectively, of the primary defect; and c) applying a third layer of running continuous sutures in the fascia along the primary defect, wherein the second layer includes at least two of the plurality of vertical mattress sutures applied to non-damaged tissue superior to the primary defect and at least two of the plurality of vertical mattress sutures applied to non-damaged tissue inferior to the primary defect along the axis of the primary defect.

2. The method of claim 1, wherein the suturing method is used for repairing hernia comprised of inguinal, femoral, diaphragmatic, umbilical, ventral and incisional hernia.

3. The method of claim 1, wherein the plurality of vertical mattress sutures are applied perpendicularly to the axis of the primary defect.

4. The method of claim 1, wherein the third layer of running continuous sutures comprises a first running continuous suture running from non-damaged tissue superior to the primary defect and a second running continuous suture running from non-damaged tissue inferior to the primary defect, wherein the first running continuous suture and the second running continuous suture meet and are tied together.

5. The method of claim 4, wherein the third layer extends superiorly and inferiorly to non-damaged tissue at least two inches beyond the primary defect.

6. The method of claim 1, wherein the third layer of running continuous sutures are stitched in between the plurality of vertical mattress sutures of the second layer.

7. The method of claim 1, wherein the first layer is composed of a first non-absorbable material, the second layer is composed of a second non-absorbable material and the third layer is composed of a third non-absorbable material.

8. The method of claim 7, wherein the first, second and third non-absorbable materials can be independently selected from the group consisting of polypropylene, polyester, nylon, polyvinylidene fluoride (PVDF), polyethylene, blends of polyvinylidene fluoride and polyvinylidene fluoride-co-hexafluoropolypropylene, and polyethylene terephthalate.

9. The method of claim 1, further comprising a recurrence rate of not more than 4% for hernia repair without surgical mesh.

10. A method for repairing hernia without surgical mesh using multi-layered suturing comprising:

a) applying a first layer of running continuous sutures to close a primary defect in a fascia of the hernia, wherein the primary defect has a superior end and an inferior end and an axis formed thereby, and wherein the axis has a superior pole region that is located entirely in non-damaged tissue beyond the superior end of the primary defect and an inferior pole region that is located entirely in non-damaged tissue beyond the inferior end of the primary defect, and wherein the axis has a mid-pole region between the superior end and the inferior end of the primary defect;

b) applying a second layer comprising a plurality of vertical mattress sutures, wherein the plurality of vertical mattress sutures are applied along and across the axis of the primary defect in the fascia of the hernia, and wherein the second layer extends from the superior pole region to the inferior pole region, and wherein the superior pole region extends at least two inches beyond the superior end of the primary defect and wherein the inferior pole region extends at least two inches beyond the inferior end of the primary defect, and wherein the superior pole region includes at least two of the plurality of the vertical mattress sutures of the second layer and the inferior pole region includes at least two of the plurality of the vertical mattress sutures of the second layer; and c) applying a third layer of sutures along the axis of the primary defect in the fascia of the hernia, wherein the third layer of sutures are applied by suturing a first suture from the superior pole region to the mid-pole region and suturing a second suture from the inferior pole region to the mid-pole region, and tying the first suture and the second suture together at the mid-pole region.

11. The method of claim 10, wherein the suturing method is used for repairing hernia comprising of umbilical, ventral and incisional hernia.

12. The method of claim 10, wherein the superior pole region extends approximately three inches beyond the superior end of the primary defect and wherein the inferior pole region extends approximately three inches beyond the inferior end of the primary defect.

13. The method of claim 10, wherein the superior pole region extends approximately two to three inches beyond the superior end of the primary defect and wherein the inferior pole region extends approximately two to three inches beyond the inferior end of the primary defect.

14. The method of claim 10, wherein the third layer of sutures is stitched in between the plurality of vertical mattress sutures of the second layer.

* * * * *